US005258017A

United States Patent [19]

Myers et al.

[11] Patent Number: 5,258,017

[45] Date of Patent: Nov. 2, 1993

[54] TRACTION DEVICE

[75] Inventors: Harold Myers, 1 Egerton Grove, Walkden, Worsley, Manchester; M28 5LH, United Kingdom; Simon Whigham, Blackburn, United Kingdom

[73] Assignee: Harold Myers, Manchester, United Kingdom

[21] Appl. No.: 768,898

[22] PCT Filed: May 8, 1990

[86] PCT No.: PCT/GB90/00705

§ 371 Date: Jan. 9, 1992

§ 102(e) Date: Jan. 9, 1992

[87] PCT Pub. No.: WO90/13279

PCT Pub. Date: Nov. 15, 1990

[30] Foreign Application Priority Data

May 9, 1989 [GB] United Kingdom ................. 8910616

[51] Int. Cl.[5] ................................................ A61F 5/00

[52] U.S. Cl. .................................... 606/241; 482/131; 602/36

[58] Field of Search ................. 482/91, 124, 125, 131; 273/DIG. 19; 602/19, 36; 606/241; 128/31

[56] References Cited

U.S. PATENT DOCUMENTS

| | | | |
|---|---|---|---|
| 359,903 | 3/1887 | Stephens . | |
| 412,999 | 10/1889 | Turney | 128/31 |
| 504,598 | 9/1893 | Leyda | 128/31 |
| 930,768 | 8/1909 | Kelly | 128/31 |
| 2,097,376 | 10/1937 | Marshman | 482/124 |
| 2,475,003 | 7/1949 | Black . | |
| 2,966,906 | 1/1961 | Wiltrout | 602/36 |
| 3,162,442 | 12/1964 | Karlik | 482/124 |
| 3,986,499 | 10/1976 | Fischer . | |
| 3,999,752 | 12/1976 | Kupperman et al. | 482/131 |
| 4,010,744 | 3/1977 | Boyen | 602/36 |
| 4,407,274 | 10/1983 | Goodley . | |
| 4,441,707 | 4/1984 | Bosch | 482/131 |
| 4,456,249 | 6/1984 | Calabrese | 482/124 |
| 4,580,554 | 4/1986 | Goodley . | |
| 4,641,637 | 2/1987 | Rosen . | |
| 4,685,671 | 8/1987 | Hagerman et al. | 482/124 |
| 4,865,022 | 9/1989 | Gorsen . | |
| 5,001,791 | 3/1991 | Toso | 602/19 X |

FOREIGN PATENT DOCUMENTS

| | | | |
|---|---|---|---|
| 0247684 | 12/1987 | European Pat. Off. . | |
| 1491184 | 3/1969 | Fed. Rep. of Germany . | |
| 2000045 | 7/1971 | Fed. Rep. of Germany | 602/19 |
| 150956 | 11/1931 | Switzerland . | |

*Primary Examiner*—Richard J. Apley
*Assistant Examiner*—Linda C. M. Dvorak
*Attorney, Agent, or Firm*—Fisher, Christen & Sabol

[57] ABSTRACT

A traction device for relieving back pain has a flexible strip (1) which is held around a person's waist by a belt (2). Two adjustable straps (3) are attached at one end to the belt (2) and are provided with stirrup loops (12) at their opposite ends. The stirrup loops (12) fit around the person's feet and the person can self-apply a traction force to his spinal column by extending his knees.

4 Claims, 1 Drawing Sheet

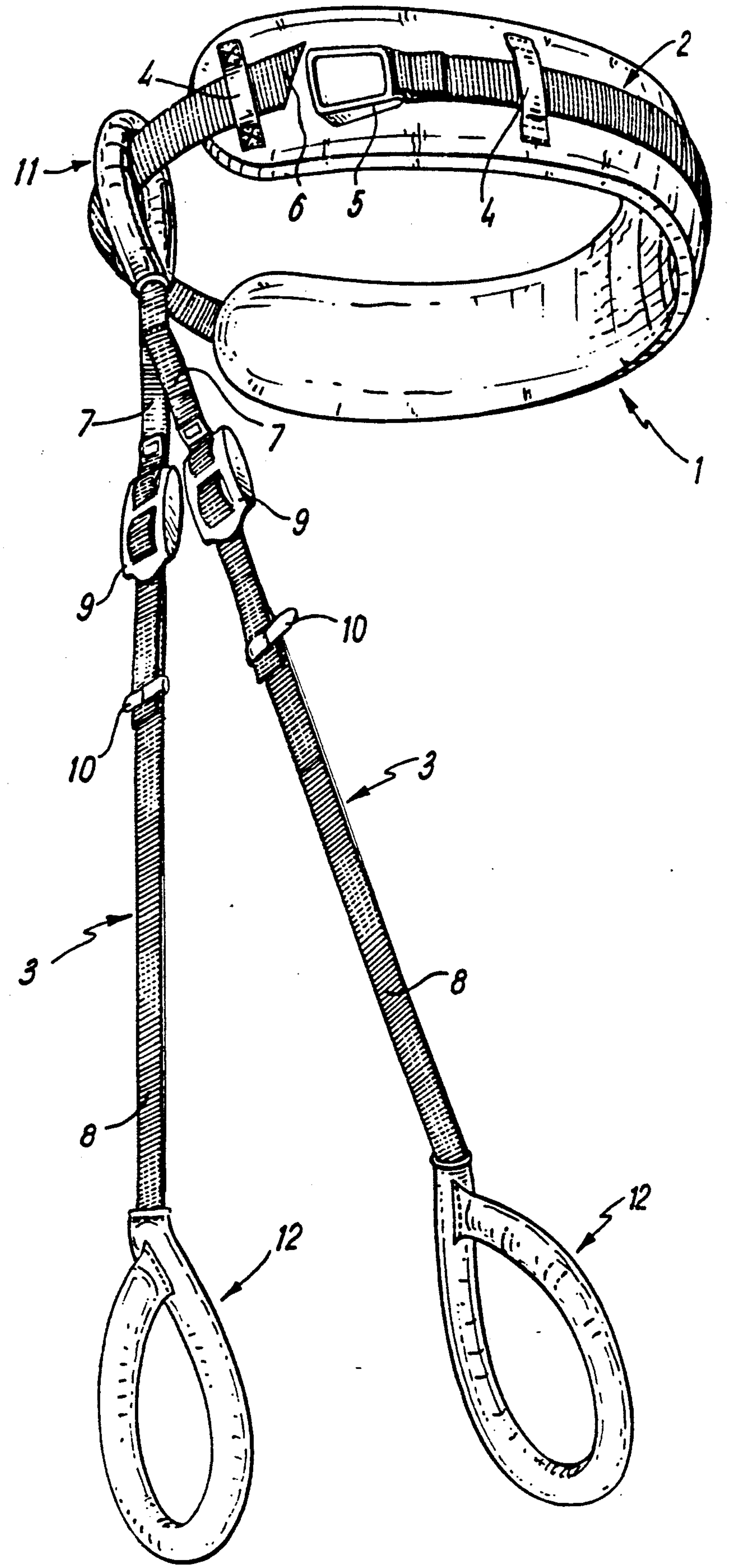
2
4
4
11
6
5
7
7
1
9
9
10
10
3
3
8
8
12
12

TRACTION DEVICE

FIELD OF THE INVENTION

This invention relates to a traction device for achieving the relief of back pain by providing distraction of the segments of the lumbar vertebrae.

BACKGROUND OF THE INVENTION

Apparatus for the relief of back pain is known, however, such apparatus is commonly relatively large and complicated and may require expert assistance for proper use thereof.

Accordingly it is usual for a patient to attend a specialist clinic or the like for treatment.

An object of the present invention is to provide a simple traction device with which it is possible for a person to self administer treatment with the minimum of assistance.

SUMMARY OF THE INVENTION

According to the present invention therefore there is provided a traction device for achieving the relief of back pain comprising a body part adapted to be secured around a person's waist, two elongate traction parts connected thereto having support parts at ends remote from said body part adapted to engage the person's feet and adjustment means for adjusting the length of said traction parts, whereby the person can apply a traction force to his spinal column by extending his knees.

With this arrangement it is possible for back pain to be abolished or relieved by a person in a particularly simple and convenient manner without the necessity for specialised treatment or appreciable expert assistance. Large complicated apparatus is not required and indeed the device may be of a size and shape suited to ready carrying by hand or even suited to stowing in a handbag.

Preferably the body part is adapted to be attached to a belt which can be secured around the person's waist. Said body part may be adapted to engage the belt by way of a plurality of retainers and may be arranged to engage the belt in such a manner that a part of the belt is exposed or free of the body part i.e. such that the body part is arranged to extend only partially around the person's body. Suitably the body part may comprise a flexible strip formed e.g. from a padded or resilient material or the like.

Said traction parts may be connected to the body part by way of coupling means and said coupling means may be arranged to engage the abovementioned exposed belt part. Said coupling means may comprise a loop or other device which permits sideways movement relative to the body part e.g. sliding movement along the said exposed belt part for positional adjustment purposes.

Each traction part may be connected to a separate said coupling means or the two traction parts may be interconnected with the same coupling means.

Said support parts may comprise stirrup loops and may be formed integrally with the traction parts. These loops may incorporate padding or the like for comfort.

Said traction parts may be formed as single lengths or alternatively may be formed as two lengths which are movably interconnected for length adjustment purposes. Thus, for example, the traction parts may each be formed from two straps e.g. of webbing material joined by a buckle or other similar adjustment device. It may even be possible to form the two traction parts wholly or partially integrally e.g. by using a single strap (or a branded strap) or the like.

BRIEF DESCRIPTION OF THE DRAWINGS

The invention will now be described further by way of example only and with reference to the accompanying drawing the single FIGURE of which shows a perspective view of one form of traction device according to the invention.

DETAILED DESCRIPTION OF THE INVENTION

The traction device shown in the drawing comprises a body harness including a body part 1, a belt 2 which is arranged to secure the body harness part around a person's waist and two traction parts 3 which are attached to and are suspended from the belt 2.

The body part 1 comprises an elongate foamed plastics padding structure which is completely enclosed by a cover of any suitable material. For example the structure may be enclosed within a stitched-up fabric cover. Four retaining strips or loops 4 are attached to one side of the harness cover in equispaced positions along the length thereof. The strips 4 are secured to the harness cover by stitching at opposite ends. The outer retaining strips 4 i.e. those closest to the ends of the body part 1 are attached to the harness cover more securely than the other strips 4 by for example extra stitching or other suitable means. This is required in order to provide adequate strength when the device is in use as described below.

The belt 2 comprises an elongate strip of webbing material having a buckle 5 attached to one end for selective engagement along the length of the belt. The other end 6 of the belt 2 is shaped such that it is easily locatable in the buckle 5.

The belt 2 is of greater length than the body part 1 for a reason which will become apparent later and is suitably dimensioned to fit through the retaining strips 4.

Each traction part 3 comprises two webbing strips 7, 8 connected end to end by a buckle 9 and a retaining strap 10. The free end portions of respective first webbing strips 7 of the two traction parts 3 are stitched together and are integrated with a coupling loop 11. The coupling loop comprises a loop formed by stitching the webbing material at the end region of one of the traction part strips 7 and is enclosed within a tube of a suitable soft, protective fabrics material.

The free end portion of a respective secured said webbing strip 8 of each traction part 3 is integrated with a foot stirrup 12 which comprises a loop formed by stitching the webbing material of the strip 8. The loop is twisted in the manner of a Möbius strip and is enclosed within a tube of soft, protective fabrics material with a strip of foam plastics padding material incorporated within the tube for increased comfort.

The buckle 9 of each traction part is of the 'ladder lock' type which is securely fixed to the first webbing strip 7 (by stitching of the end of such strip), the adjacent end portion of the second strip 8 being looped through the buckle 9. The free end of the strip 8 is held captive by the retainer strap 10.

In use the belt 2 is fed through the retainers 4 of the body part 1 and through the coupling loop 11. The buckle 5 on the body belt 2 is located between two of the retainers 4 on the body part 1 and is attached to the free end 6 of the belt 2 in such a position that the aperture defined by the belt 2 and body part 1 is large enough to pass over the head, shoulders and trunk of a person to be treated.

The second webbing strips 8 of the traction parts 3 are engaged with the respective buckles 9.

The device so assembled is placed over the person's head and is pulled down over his head, shoulders and trunk to the midriff region. The body harness is tightened around his waist, by appropriate adjustment of the belt 2 with the buckle 5, in the region about the person's iliac crests. The person then lies in a prone position on a suitable flat surface and with the assistance of a second person the foot stirrups 12 are placed around his feet with his knees in the semi-flexed position. The second person then adjusts the buckles 9 on the traction parts 3 to alter the lengths of the traction parts. This is achieved by pulling the second webbing strips 8 either further through the buckles 9 or by releasing the strips 8. This adjustment has the effect of altering the amount of traction that will be applied to the lower back, when the person extends his knees fully (i.e. when he straightens out his legs).

The person undergoing treatment can assist the second person by advising him as to when the pain is relieved. The traction applied is in the form of a cephalic-caudal force which acts to provide a distraction of the segments of the lumbar vertebrae. The person is thus able to control the traction applied by extension of his knees as a result of the bilateral and simultaneous contractions of his quadriceps muscles. Furthermore the person is able to control the time for which the force is applied himself in accordance with the pain felt, and is guided by the proprioceptive receptors in the segments thus distracted. The device therefore gives the possibility of careful control of force application on the basis of 'feed back control'.

Removal of the device is simply a matter of the person flexing his knees, removing his feet from the foot stirrups 12 and then removing the body belt 2 and body part 1.

With this embodiment it is possible for back pain to be abolished or relieved in a simple and convenient manner without the necessity for specialised treatment, although of course it is desirable for an expert opinion to be obtained first as to the nature of the musculoskeletal problem.

It is of course to be understood that the invention is not intended to be restricted to the details of the above embodiment which are described by way of example only. Also, although reference is made to a male user of the device it is of course to be appreciated that it is also suitable for female users.

We claim:

1. A traction device for achieving the relief of back pain comprising:

(a) a body harness including a belt for encircling and for being secured around a person's waist, the belt carrying a padded flexible strip which is held around the person's waist by means of said belt being attached to the flexible strip, said flexible strip being of greater width than the belt and extending only partially around the person's body to provide a belt part which is free of the flexible strip at one side of the body harness, (b) two elongate traction parts each connected at one of their ends by coupling means to a single point of said belt part which is free of the flexible strip, at one side of the said body harness and each of their other ends having a single stirrup support loop adapted to engage the person's feet, said coupling means being sideways adjustable relative to said belt part, said traction parts each comprising a buckle between said one end and said other end, the length of each traction part being adjustable by means of the buckle, the length of each traction part being adjusted to a fixed length so that when the person's knees are extended from a flexed position to straighten the person's legs, traction is applied by said extension in the form of a cephalic-caudal force which acts to provide a distraction of the segments of the lumbar vertebrae for relieving back pain.

2. A device according to claim 1 wherein the belt is attached to the flexible strip by means of retaining strips or loops.

3. A device according to claim 1 wherein the coupling means comprises a loop which engages said belt.

4. A device according to claim 1 wherein the two parts are connected to the belt part with a common said coupling means.

* * * * *